United States Patent [19]
Greene

[11] Patent Number: 5,201,774
[45] Date of Patent: Apr. 13, 1993

[54] PROSTHETIC VALVE SYSTEM AND PROCESS FOR SEALING A SOCKET

[75] Inventor: Ted J. Greene, La Canada, Calif.

[73] Assignee: United States Manufacturing Company, Pasadena, Calif.

[21] Appl. No.: 749,258

[22] Filed: Aug. 23, 1991

[51] Int. Cl.⁵ .............................................. A61F 2/80
[52] U.S. Cl. ....................................... 623/34; 623/37; 623/901; 264/275; 264/274
[58] Field of Search .................... 623/33, 34, 37, 66, 623/901, 35, 36; 251/359; 285/3; 264/274, 275, 222, DIG. 30

[56] References Cited

U.S. PATENT DOCUMENTS

| | | | |
|---|---|---|---|
| 2,530,285 | 11/1950 | Catranis | 623/33 X |
| 4,010,052 | 3/1977 | Edwards | 264/275 X |
| 4,106,745 | 8/1978 | Carrow | 264/275 X |
| 4,370,791 | 2/1983 | Wilson | 264/274 X |

FOREIGN PATENT DOCUMENTS 2825097  3/1980  Fed. Rep. of Germany ...... 264/275

Primary Examiner—Randall L. Green
Assistant Examiner—D. Willse
Attorney, Agent, or Firm—Christie, Parker & Hale

[57] ABSTRACT

A valve housing for a prosthetic socket has a secure leak-free mechanical interlock formed between the valve housing and the socket. A valve housing has an opening for receiving a removable relief valve. A plug separate from the relief valve is first removably secured in the opening in the valve housing, followed by fastening the valve housing and the plug to a model defining the shape of the finished socket. The fastened plug closes off the opening through the valve housing. The exterior wall of the valve housing has a mechanical interlock, preferably a pair of O-rings extending circumferentially around the body of the valve housing. A thermoplastic material is drawn down over the plugged valve housing and around the interlock device to cover the valve housing and the model. In one embodiment, a releasable pressure clamp is applied to the softened plastic that extends circumferentially around the exterior of the valve housing. The clamp applies circumferential pressure inwardly to the plastic as it cools to form a secure bond and interlock between the plastic and the O-ring-sealed valve housing. Any plastic covering the plug can be removed and the plug is removed from the valve housing, leaving an annular lip or locking flange of the plastic material on an annular end face of the valve housing, which retains the valve against movement from downward pressure and avoids leakage of air between the valve housing and the plastic socket.

15 Claims, 5 Drawing Sheets

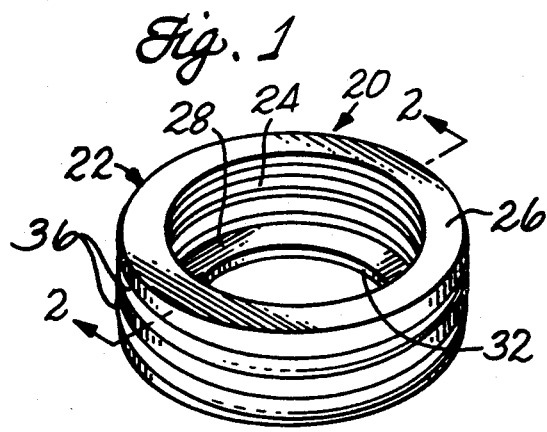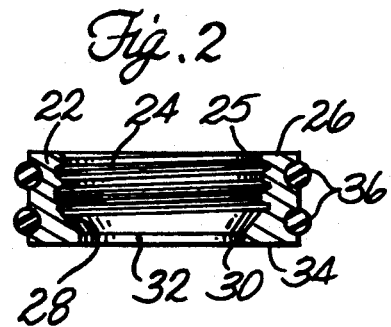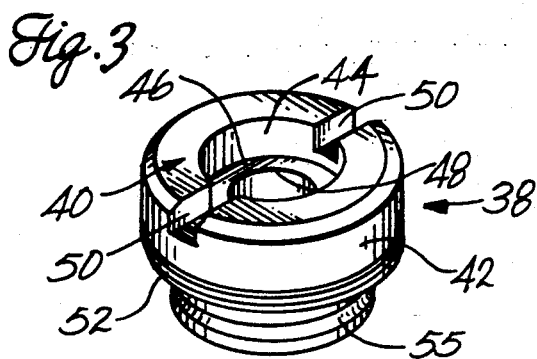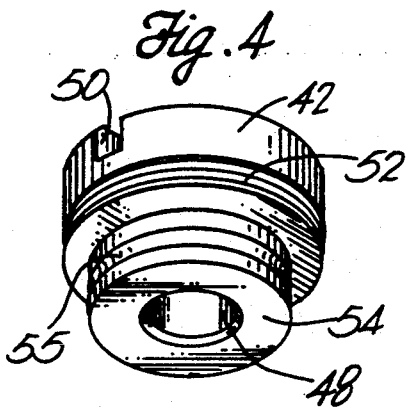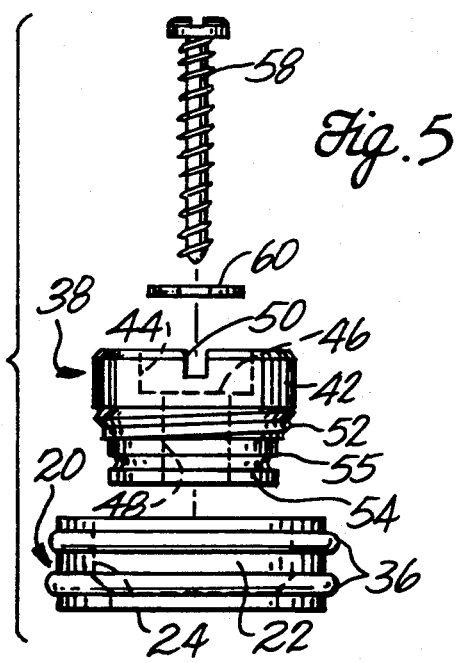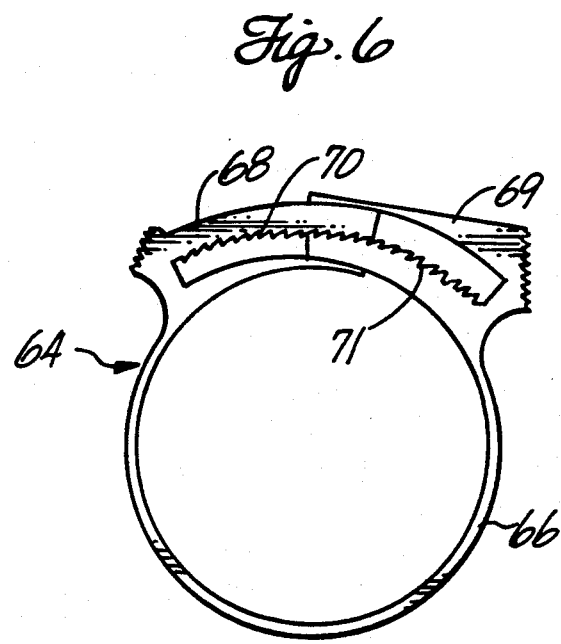

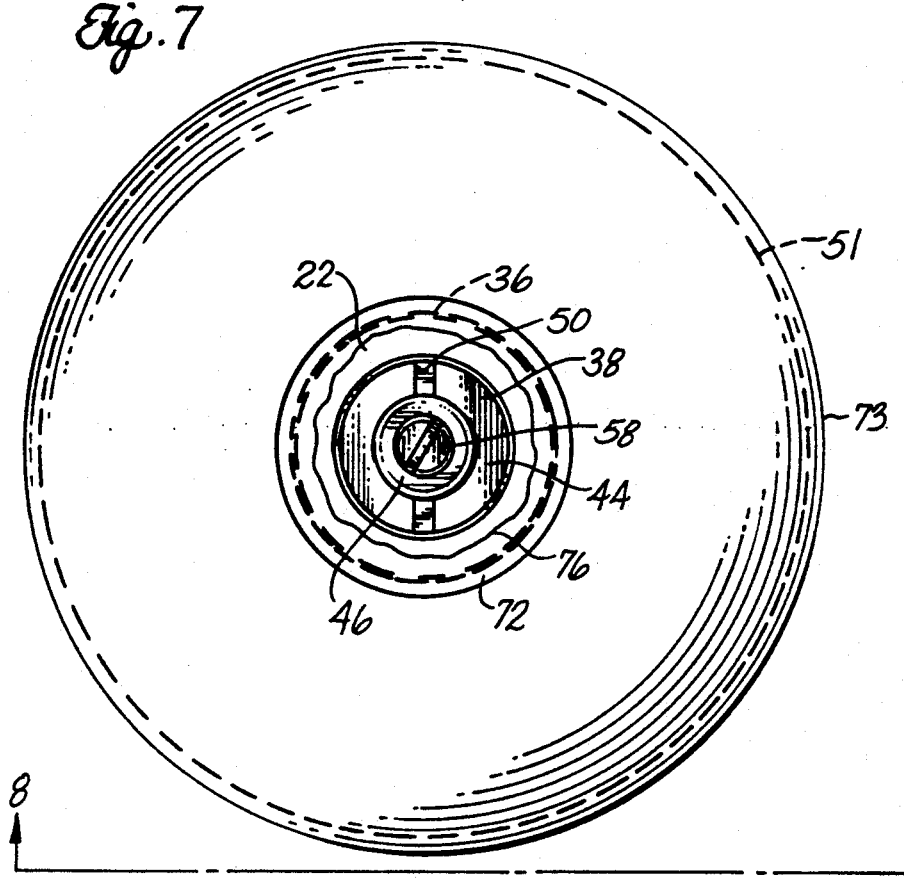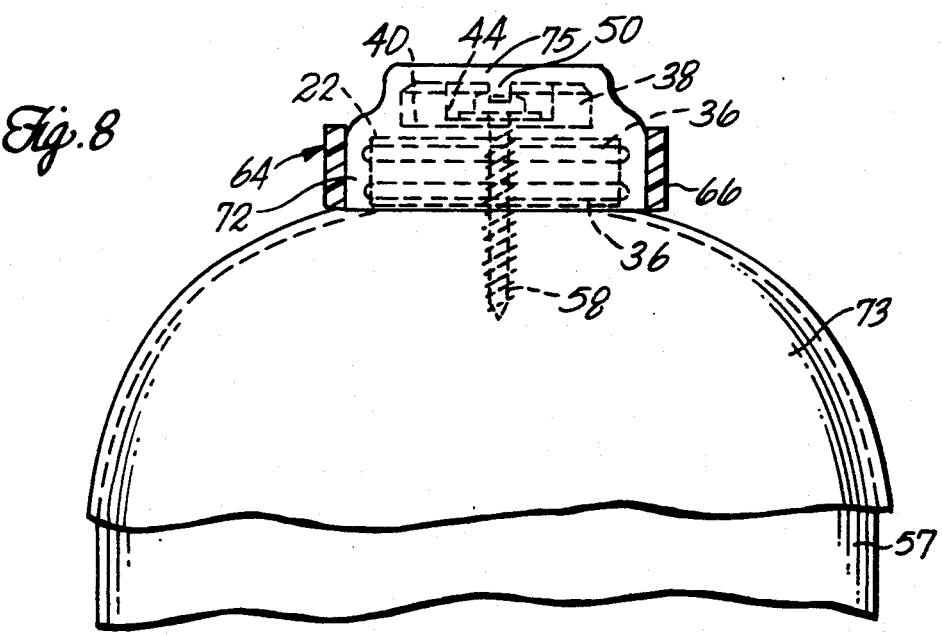

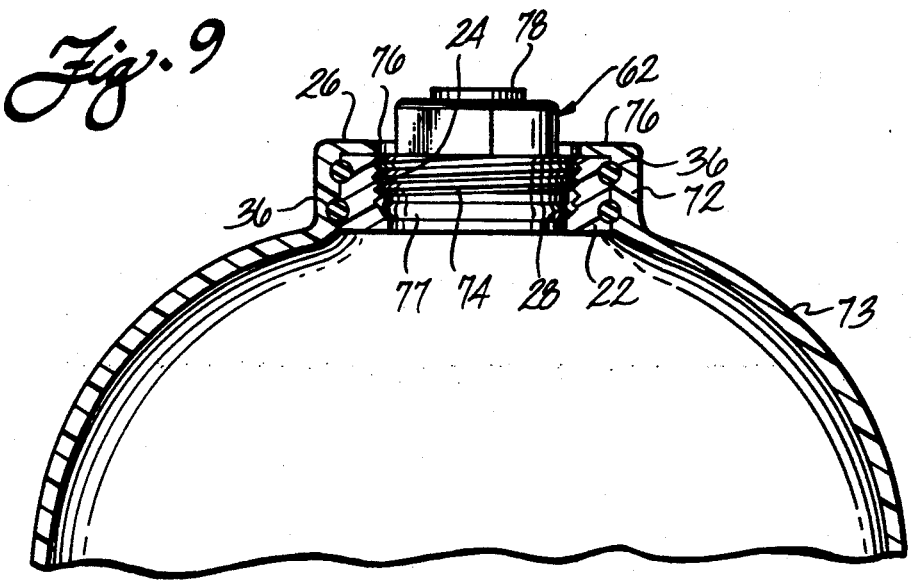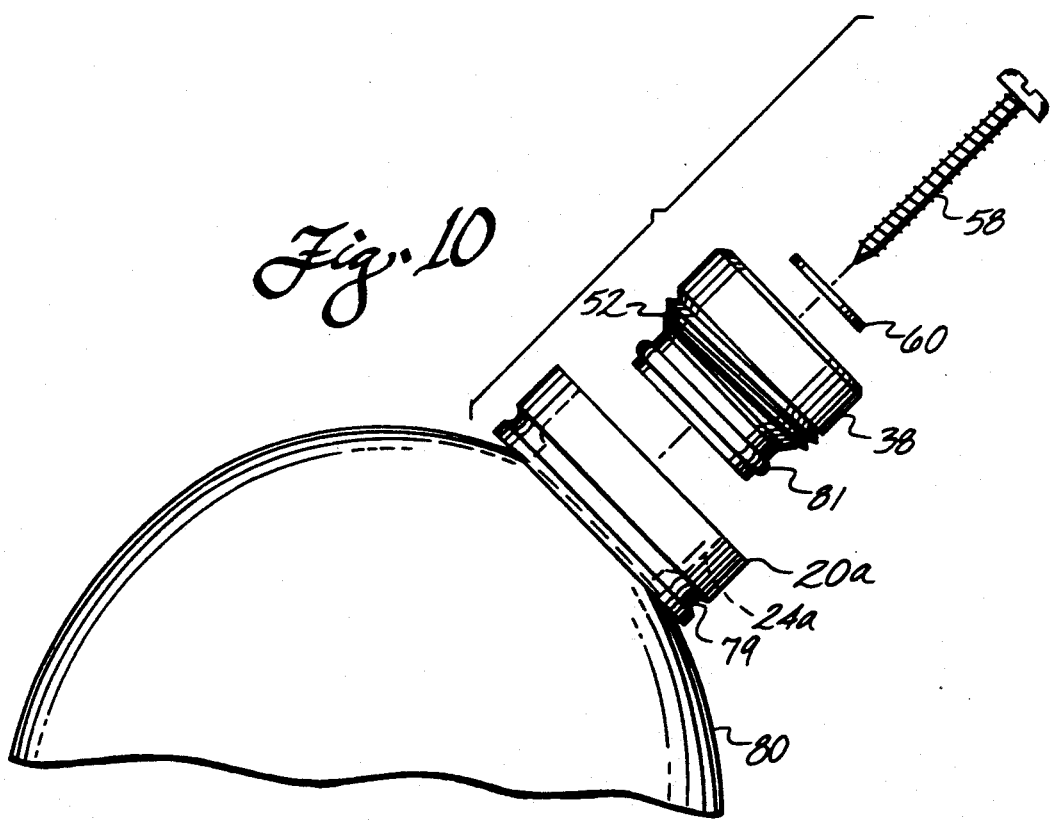

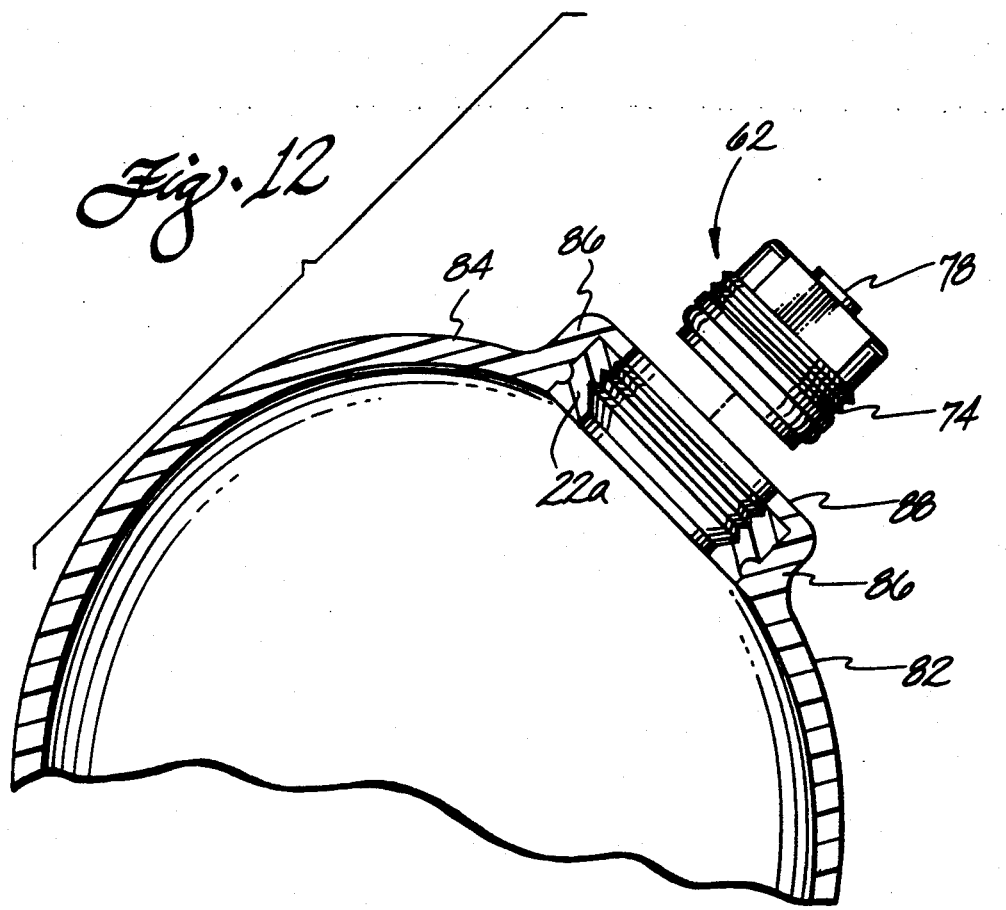

PROSTHETIC VALVE SYSTEM AND PROCESS FOR SEALING A SOCKET

FIELD OF THE INVENTION

This invention relates to prosthetic appliances, and more particularly, to a leak-free prosthetic valve system for an above-knee socket.

BACKGROUND OF THE INVENTION

After an amputation, and once healing is completed, a permanent or "definitive" prosthesis is assembled by the prosthetic. The permanent prosthesis for an above-knee amputation includes a socket made from a cast that matches the shape of the stump. A prosthetic limb attached to the bottom of the socket typically carries a knee joint and a prosthetic foot.

There is a constant need to provide an above-knee prosthesis which is comfortable at all times when in use. To this end, it has been common for a liner to be worn by a patient to protect the skin from direct contact with the inside of the socket, where discomfort is often a problem. Recently, the use of softer, more flexible plastic materials for the socket has avoided the need for wearing a liner. In either event, the socket is custom-made with a removable valve installed in a housing in the bottom. The value is removed to allow the prosthetic limb wearer to don the prosthesis through a "pulling-in" process which involves threading a tubular knit pull sock through the valve hole after previously slipping the opposite end over the residual limb. A one-way relief valve which can be operated by finger pressure to exhaust any air entrapped inside the socket is installed in the housing after donning. In this way, the user can use the air relief valve to exhaust residual air from the socket after donning the prosthesis and at any time thereafter to relieve discomfort caused by entrapped air between the skin and the inside of the socket.

There have been several prior art attempts to provide a secure, leak-free valve system for a prosthetic socket, but none has proved entirely satisfactory. The problem of developing a leak-free housing is particularly difficult when using the softer, more flexible vacuum-formed plastics, such as polyethylene, for the socket material. These materials are desirable for their comfort, but they can be difficult to bond to a rigid valve housing in a way that maintains the seal under pressures applied during constant use.

In one prior art valve system, a thin rubbery gasketing material is applied around the exterior of a valve housing attached to the cast or model. When the plastic socket material is vacuum-formed over the valve housing and the model, the gasketing material is intended to form a seal between the valve housing and the socket. However, during use, this valve system is prone to leak air between the hard plastic valve housing and the flexible polyethylene socket.

Another prior art valve system uses a hard plastic valve housing with vertical notches in its exterior surface and a horizontal O-ring near the bottom of the housing. The notches and O-ring are intended to form a mechanical interlock with the vacuum-formed socket, but this valve system also is prone to leaking between the valve housing and the plastic socket.

More recently, a valve housing has been made with a downwardly tapered, conical outer surface and an O-ring located in the conical surface at the interface for interlocking with the vacuum-formed plastic. This arrangement also does not appear to provide the mechanical interlock necessary for a secure leak-free valve during long term use of the socket.

SUMMARY OF THE INVENTION

Briefly, the present invention provides a valve housing for a prosthetic socket in which a secure, leakfree mechanical interlock is formed between the valve housing and the socket. The invention is characterized by a set of components assembled according to a method of this invention to form the leak-free valve system.

In one embodiment, the invention includes a valve housing having an opening for receiving a removable air relief valve. A dummy plug, which is separate from the relief valve, also is removably received in the opening of the valve housing. The plug is first installed in the valve housing, followed by fastening the valve housing and the installed plug to the model which defines the shape of the finished socket. The fastened plug closes off but does not seal the opening through the valve housing. The exterior wall of the valve housing has a mechanical interlock device on a portion of the valve housing wall that extends circumferentially around the body of the valve housing and therefore around the opening through the housing. The mechanical interlock, in one embodiment, comprises a pair of O-ring gaskets seated in the exterior wall of the valve housing and spaced apart along the axis of the valve opening. A thermoplastic material for forming the socket is drawn down over the plugged valve housing and around the interlock device on the valve housing to cover the model and conform to the shape of the model. In one embodiment, a releasable pressure clamp is applied to the softened plastic that extends circumferentially around the exterior of the plugged valve housing and its interlock device. The clamp applies circumferential pressure inwardly to the plastic as it cools to form a secure bond between the plastic and the interlock device on the exterior of the valve housing. Any plastic covering the plug can be removed after the plastic hardens. The plug is then removed from the valve opening, and the socket is removed from the model. An annular lip of hardened plastic covers the outer end face of the valve housing. This lip produces a locking flange that retains the valve housing and resists its movement from downward pressure and avoids leakage of air between the valve housing and the plastic socket. The standard one-way air relief valve then can be installed in the leak-free valve housing.

These and other aspects of the invention will be more fully understood by referring to the following detailed description and the accompanying drawings.

BRIEF DESCRIPTION OF THE DRAWINGS

FIG. 1 is a top perspective view of a valve housing.

FIG. 2 is a cross-sectional view taken on line 2—2 of FIG. 1.

FIG. 3 is a top perspective view of a plug for the valve housing.

FIG. 4 is a bottom perspective view of the plug.

FIG. 5 is an exploded side elevation view showing an assembly of components for plugging the valve housing and fastening the plugged valve housing to a model.

FIG. 6 is an elevation view showing a circumferential pressure clamp.

FIG. 7 is a top view of a vacuum formed plastic shell formed over the plugged valve housing.

FIG. 8 is a side elevational view, partly in cross-section, taken on line 8—8 of FIG. 7.

FIG. 9 is an enlarged cross-sectional view illustrating a completed leak-free valve assembly.

FIG. 10 is a side elevational view, exploded in part, to show components of a plugged valve housing secured to a model.

FIG. 12 is an enlarged cross-sectional view, exploded in part, and showing a completed leak-free valve housing and a valve.

DETAILED DESCRIPTION

Figure 11:
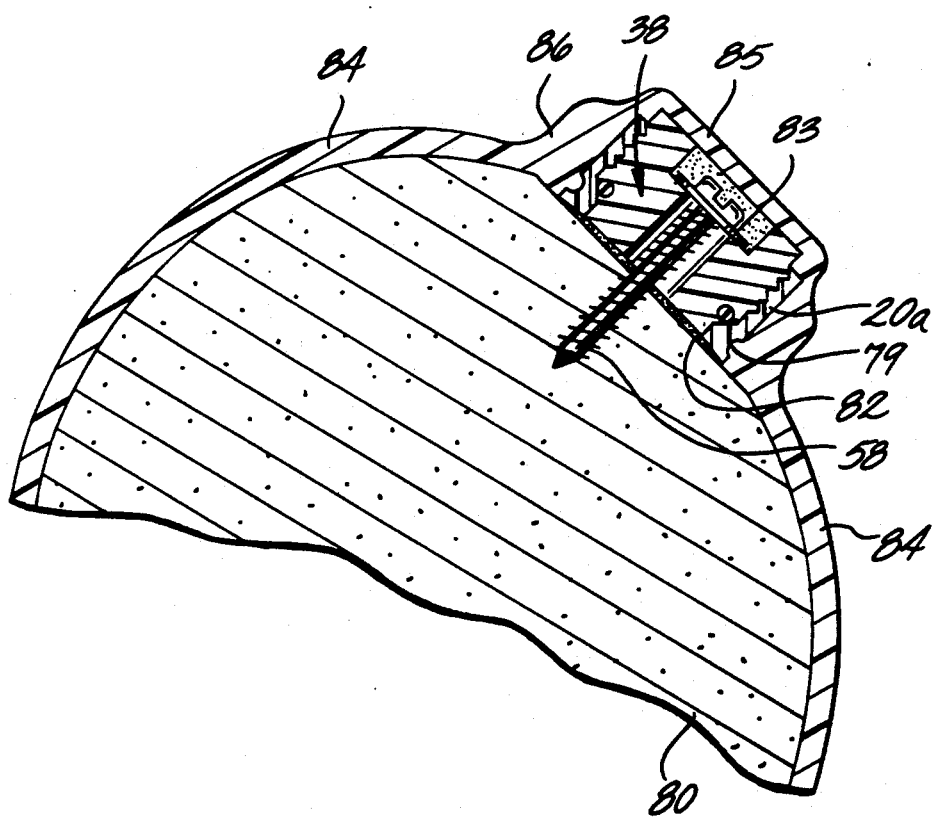
FIG. 11 is a cross-sectional view of the plugged valve housing following vacuum forming of a plastic socket.

FIGS. 1 and 2 illustrate a valve housing 20 according to principles of this invention. The valve housing is a component of an air relief valve molded to a prosthetic socket described below. The valve housing 20 has a cylindrical ring shaped body 22 with an internally threaded circular bore 24 extending through the housing. A circular upper opening 25 faces outwardly through a flat annular upper end face 26 of the valve housing. The screw threaded bore 24 extends from most of the depth of the housing below the opening 25 and is stepped up near its bottom to form an angularly inclined annular shoulder 28 below the threads. A thin upright annular wall 30 extends below the angular shoulder and opens through a circular lower opening 32 having a diameter slightly less than the diameter of the upper opening 25. The bottom of the housing has a slightly concave end face 34. The end faces 26 and 34 of the housing are parallel to one another, and the openings in the top and bottom of the housing are aligned on a common axis through the center of the housing. The exterior annular wall of the valve housing has a pair of vertically spaced apart and parallel annular recesses surrounding the axis through the housing. The annular recesses mount a corresponding pair of spaced apart and parallel elastomeric O-ring seals 36 extending circumferentially around the body of the valve housing in planes spaced apart along the length of the central axis through the valve housing. The O-ring seals protrude from the cylindrical outer wall of the housing, as shown best in FIG. 2. The valve housing can be made of any desired material such as aluminum, stainless steel, or a hard plastic such as Delrin.

FIGS. 3, 4, and 5 illustrate a dummy plug 38 which screws into the internally threaded bore 25 of the valve housing. The plug has an annular body 40 which includes an upright annular shoulder 42 at its upper end surrounding a large circular bore 44 that opens through the top of a central opening through the plug. The bore 44 is stepped up at about the middle of the plug to form a horizontal annular shoulder 46 below the large bore 44. A small diameter bore 48 extends through the remaining lower portion of the opening through the plug below the annular shoulder 46. A pair of slots 50 in the annular upper end face of the upper shoulder 42 provide a means for receiving a tool (not shown) for rotating the plug when fastening it or removing it from the internally threaded housing. The plug further includes an externally threaded wall 52 below the upper shoulder 42. The screw threads at 52 have the same outside diameter as the outer wall of the upper shoulder 42. The outer surface of the plug tapers downwardly and inwardly below the threaded section 52 to form a smaller diameter annular lower portion 54. An annular recess 55 is formed in the exterior wall of the lower portion 54 of the plug.

As shown best in the exploded view of FIG. 5, the valve housing 20 and the plug 38 are both adapted for fastening to a plaster model (not shown) that conforms to the shape of a prosthetic socket. The plug screws into the opening through the valve housing by engaging the threads 52 of the screw plug with the threaded opening 24 in the valve housing. The valve housing is placed against the model, the plug is screwed into the valve housing, and a wood screw 58 and washer 60 are then used to fasten the plug and valve housing to the model. A pilot hole, not shown, is first drilled in the model at the point where the valve housing is to be attached to the model. The screw 58 is then screwed into the pilot hole. The washer 60 rests against the top of the shoulder 46 in the plug and the screw passes through the bore 48 in the valve housing, into the pilot hole, and is tightened against the top of the washer to rigidly affix the plug and valve housing to the desired position on the model. There is a gap between the washer and plug to allow vacuum to pull plastic against the plug face. The plug 42 (1) fills the housing so no plastic will be drawn into the threads, (2) allows for firm attachment of the housing to the model (with screw and washer), (3) does not seal, but allows a vacuum to be pulled through the threads to pull plastic firmly against the housing face (see FIG. 11), and (4) provides a hole for introducing compressed air to blow a finished prosthetic socket off of the model.

EXAMPLE 1

FIGS. 6 through 9 illustrate various steps of a preferred process for securing the valve housing to a vacuum-formed thermoplastic socket formed as a thin shell on a model 57 to which the valve housing and the plug are attached. The preferred process for sealing the valve to the socket formed by the vacuum-forming techniques includes use of the valve housing 22, the plug 38, the fasteners 58 and 60, and a circumferential pressure clamp 64 shown in FIG. 6.

According to a preferred process, the plug 38 is first screwed into the valve housing 20. The valve housing and plug are located on the plaster model that simulates the shape of the above-knee socket. A pilot hole, preferably 1/8-inch in diameter, is then drilled through the center of the opening through the plug to determine the valve location. A nylon stocking (not shown) is threaded through the hole in the plug and a knot is tied in the stocking to prevent the plug from slipping off the model. The nylon is pulled down over the model, positioning the plug over the pilot hole. The screw 58 is then tightened down into the opening through the plug to rigidly affix the plug and valve housing to the model.

The thermoplastic material used to form the socket is then vacuum-formed over the model. Preferably, a sheet of plastic such as polyethylene is placed in a frame (not shown) which is placed in an oven to soften the plastic. The softened plastic and frame are then removed from the oven and placed over the top of the model so that the plastic drapes over the top of the model, and over the plugged valve housing. With the plastic draped over the top of the model and the plugged valve housing, a vacuum is then drawn on the bottom of the plastic, while in its molten or softened condition, so as to completely encase the exterior of the model and the attached valve housing and plug. The nylon will "wick" the vacuum over the entire surface of the model and allow an even pull all the way to the end where the valve housing is installed. If no nylon or air channel to the valve area is provided the plastic can seal off against the model and prevent pulling in around the valve.

While the plastic is still in its softened condition, the clamp 64 is placed around the exterior of the valve housing and tightened against the softened plastic which extends circumferentially around the O-rings on the valve housing. Referring briefly to FIG. 6, the clamp 64 has a flexible plastic outer ring 66 with a pair of jaws at 68 and 69 facing toward one another, with cooperating ratchet teeth surfaces 70 and 71 that can be engaged with one another and pushed toward each other for progressively tightening the circumferential pressure provided by the ring portion 66 of the clamp. The clamp is placed around the plastic that surrounds the valve housing, as shown best in FIG. 8, to apply a constant inward circumferential pressure to the softened plastic, pressing firmly toward the plastic as the clamp is tightened around it. As the plastic cools, the circumferential clamp pressure causes the softened plastic 72 to conform to the double O-ring outer surface of the valve housing to form an interlock between the plastic and the two O-rings 36 on the valve housing. (FIG. 8 shows the plastic completely covering the valve housing and the dummy plug. FIG. 7 shows the plastic cut away from the top of the plug.) After the plastic has cooled, the clamp is removed by sliding the teeth apart away from the model. If plastic has flowed over the teeth, preventing them from sliding, the clamp may be rotated to an area where the teeth can be easily separated. The circumferential compression force provided by the clamp during hardening of the plastic produces a mechanical bond at the interface between the plastic and the outer wall of the valve housing.

With a sharp utility knife, the piece of plastic 75 that covers the end of the plug is removed, leaving an annular lip 76 of excess plastic (see FIG. 9) covering the flat end face 26 of the valve housing. With the utility knife, the excess nylon is also removed from the center of the plug, exposing the wood screw used to fasten the plug to the model. The screw is then removed and the socket 73 may now be blown off the model, using compressed air directed through the hole in the plug, if necessary. The plug 38 is then unscrewed from the valve housing 20, using the slots 50 at the top of the plug to facilitate removing the plug.

The standard air relief valve 62 then can be screwed into the opening in the valve housing, as shown in FIG. 9, which shows the finished socket 73 and the plastic material 76 at the top of the valve housing. The vacuum formed plastic material 72 encases the cylindrical exterior side wall of the valve housing and forms a bond and mechanical interlock with the two O-rings 36 which become embedded in the wall of plastic. The annular end wall 76 of plastic that forms the lip surrounding the upper end face 26 of the valve housing cooperates with the mechanical interlock between the O-rings to securely retain the valve housing in the socket, resisting pressure during use and thereby maintaining a leak-proof seal. FIG. 9 illustrates the standard air relief valve 62 with its externally threaded outer wall 74 screwed into the opening through the valve housing. A compressible O-ring 77 at the bottom of the standard valve is tightened against the shoulder 28 in the valve housing. The standard valve also includes a spring-loaded valve element 78 which can be actuated by finger pressure to relieve air from the inside of the socket during use.

EXAMPLE 2

FIGS. 10, 11, and 12 illustrate an alternative embodiment in which principles of the invention are adapted to a process for installing a leak-free valve system in a socket made by a laminating process. In one embodiment, the laminating process is a standard process for making a hard plastic socket with a fiberglass-impregnated resin such as a polyester resin. According to the steps in this process, the site on a plaster model 80 is located and a flattened surface is formed on the model where the valve will be attached. A pilot hole, preferably a ⅛-inch in diameter, is drilled into the model in the center of where the valve will be located. The plug threads 52 on the exterior of the plug 38 are greased thoroughly with a petroleum jelly and the plug is screwed firmly into an alternative valve housing 20a. In the illustrated embodiment, this valve housing is internally threaded at 24a but does not have the double O-ring outer surface provided on the housing 20. A recess 79 is formed in the lower outer portion of the housing 20a. The exterior of the plug 38 has an O-ring 81 which seals off the passage between the plug and housing. The model 80 is then covered with a polyvinyl alcohol (PVA) bag (not shown) which is pulled over to encase the plaster model in the usual manner. A small hole is then burned in the PVA bag to access the pilot hole previously drilled in the model. Clay commonly used in these laminating techniques is placed over the bottom face of the valve housing and the plug therein, and the screw 58 is then tightened down against the face of the model. The clay is squeezed out of the space between the bottom of the valve housing and the plug and the face of the model, leaving a layer 82 of clay at the interface so that no resin can later intrude into the space between the valve housing and the model. Excess clay is then cleaned off. The remaining center hole in the plug is then filled with clay 83 over the screw head and the slot within the plug.

The prosthetic socket 84 is then made by the usual laminating techniques in which a stockinette (not shown) is pulled over the entire model with the attached valve housing and plug. The PVA bag is then placed over the outside of the stockinette and connected at its bottom to a vacuum while the top is filled with a resin, such as polyester resin, which is allowed to pass downwardly over the stockinette to impregnate the stockinette, followed by curing of the resin. FIG. 11 shows the plastic while it cures, with a layer of plastic 85 covering the attached valve housing and plug. The housing is firmly held to the model and the plug prevents resin from entering the threads. When the lamination is completed, the laminate is removed from the valve plug face. This is done by cutting off the plastic to access the screw contained in the plug, and by removing the clay that covers the screw. Compressed air then can be introduced into the center of the plug and blow off the finished socket from the model.

The plug 38 is then removed from the valve housing, leaving a raised area 86 of hardened plastic around the valve housing. The plastic forms an interlock in the valve housing recess at 79. The plastic also covers the end face of the valve housing, forming an annular raised locking flange 88 of plastic. The standard valve 62 is then installed in the valve housing.

The laminating techniques of FIGS. 11 and 12 produce the flanged locking shoulder 88 of laminate over the end wall of the valve housing, which retains the valve housing in the wall of the socket and resists leakage. In an alternative embodiment, the housing 22a can be replaced with the double O-ring housing 22 described previously. In this case, the valve housing 22 has a wider top face to produce a wider locking shoulder 88. The laminate material at 86 also forms an interlock between the two O-rings 36 along the side of the valve housing. This combination produces a leak proof interface between the valve housing and the laminate.

What is claimed is:

1. A process for making a prosthetic socket for an amputation and for sealing an air relief valve in a wall of the socket, the process comprising:

forming a rigid model having an exterior surface shaped as the interior configuration of a tubular prosthetic socket with a closed end;

fastening an annular valve housing in a fixed position on the exterior surface of the model, the valve housing having a first annular end face disposed on the exterior surface of the model and a second annular end face spaced from the model, the valve housing having an opening extending through it with a dummy plug removably disposed in the valve opening;

applying heat to a sheet of thermoplastic material for use in forming the socket, said heat being sufficient to produce a heat softened condition of the thermoplastic sheet;

thereafter placing the heat softened plastic sheet over the exterior surface of the model and over the attached valve housing and conforming the heat softened plastic sheet to the model, the valve housing, and the dummy plug, thereby forming a thin-walled tubular prosthetic socket with a closed end and having a hollow interior in the shape of the model with the valve housing encased in the thermoplastic material;

removing the socket from the model after the plastic hardens to provide a thin-walled, flexible, tubular, closed-ended socket for an amputation with the valve housing sealed in the wall of the socket;

removing the dummy plug from the valve opening, leaving an annular lip of plastic covering the second annular end face of the valve housing for providing a means of resisting axial force on the valve housing in a direction away from the inside of the socket to thereby mechanically interlock and seal the valve housing in the wall of the socket; and placing an air relief valve in the valve opening in place of the dummy plug so the air relief valve controls air flow through the valve housing from the interior of the socket.

2. The process according to claim 1 in which the value housing has an annular side wall extending axially between the first and second end faces thereof, and including placing a circumferential clamp around the annular side wall of the valve housing and around the plastic material that covers said annular side wall, when the plastic is in a softened condition, to compress the plastic material against the side wall of the valve housing while the plastic hardens.

3. The process according to claim 2 including mounting a pair of O-ring seals spaced apart along the annular side wall of the valve housing and compressing the plastic into contact with the O-ring seals to provide a mechanical interlock between the O-ring seals and the plastic compressed into contact with the valve housing between the O-ring seals.

4. The process according to claim 1 including providing a pair of axially spaced apart O-ring seals on an annular side wall of the valve housing, and interlocking the seals with the plastic covering the valve housing.

5. The process according to claim 1 including vacuum forming the heat softened plastic material to cover the model and form a built-up area of plastic around and in contact with the valve housing attached to the model.

6. The process according to claim 5 including placing a thin, tubular, knitted fabric stocking over the model prior to covering the stocking, the model and the valve housing with the plastic to enhance flow of the heat softened plastic over the model and around and into contact with the valve housing.

7. The process according to claim 5 in which the dummy plug is engaged with the hole in the valve housing to allow air leakage sufficient to draw plastic toward the valve housing under the applied vacuum.

8. The process according to claim 1 in which the valve housing has an annular side wall extending axially between the first and second end faces thereof, and including placing a circumferential clamp around the annular side wall of the valve housing and the plastic that covers said annular side wall to compress the plastic toward the valve housing to enhance forming a leak-proof seal.

9. The process according to claim 1 including fastening the valve housing to the model by a fastener extending through a passageway in the dummy plug and into the model.

10. A process for making a prosthetic socket for an amputation and for sealing an air relief valve in a wall of the socket, the process comprising:

forming a rigid model having an exterior surface shaped as the interior configuration of a tubular prosthetic socket;

fastening an annular valve housing in a fixed position on the exterior surface of the model, the valve housing having a first annular end face disposed on the exterior surface of the model, a second annular end face spaced from the model, and an annular side wall between the end faces of the housing, the valve housing having an opening extending through it with a dummy plug removably disposed in the valve opening;

applying heat to a sheet of thermoplastic material for use in forming the socket, said heat being sufficient to produce a heat softened condition of the thermoplastic sheet;

thereafter placing the heat softened plastic sheet over the exterior surface of the model and over the attached valve housing and conforming the heat softened plastic sheet to the model, the valve housing, and the dummy plug, thereby forming a thin-walled tubular socket having a hollow interior in the shape of the model with the valve housing encased in the plastic material;

placing a circumferential clamp around the annular side wall of the valve housing and the plastic material that covers said annular side wall to compress the plastic material against the side wall of the valve housing to enhance bonding of the plastic to the valve housing;

removing the socket from the model after the plastic hardens to provide a thin-walled, flexible, tubular socket for an amputation with the valve housing sealed in the wall of the socket;

removing the dummy plug from the valve opening, leaving an annular lip of plastic covering the second annular end face of the valve housing for providing a means of resisting axial force on the valve housing in a direction away from the inside of the socket to thereby mechanically interlock and seal the valve housing in the wall of the socket; and placing an air relief valve in the valve opening in place of the dummy plug so the air relief valve controls air flow through the valve housing from the interior of the socket.

11. The process according to claim 10 including mounting a pair O-ring seals spaced apart along the annular side wall of the valve housing and compressing the plastic into contact with the O-ring seals to provide a mechanical interlock between the O-ring seals and the plastic compressed into contact with the valve housing between the O-ring seals.

12. The process according to claim 10 including vacuum-forming the heat softened plastic material to cover the model and form a built-up area of plastic around the valve housing attached to the model.

13. The process according to claim 12 in which the dummy plug is engaged with the hole in the valve housing to allow air leakage sufficient to draw plastic toward the valve housing under the applied vacuum.

14. The process according to claim 10 including placing a thin, tubular, knitted fabric stocking over the model prior to covering the stocking, the model, and the valve housing with the plastic to enhance flow of heat softened plastic over the model and around the valve housing.

15. The process according to claim 10 including fastening the valve housing to the model by a fastener extending through a passageway in the dummy plug and into the model.

* * * * *